United States Patent [19]

Way

[11] 4,391,617
[45] * Jul. 5, 1983

[54] PROCESS FOR THE RECOVERY OF VAPORIZED SUBLIMATES FROM GAS STREAMS

[76] Inventor: Peter F. Way, P.O. Box 276, Boxford, Mass. 01921

[*] Notice: The portion of the term of this patent subsequent to Feb. 24, 1998, has been disclaimed.

[21] Appl. No.: 216,934

[22] Filed: Dec. 16, 1980

Related U.S. Application Data

[63] Continuation-in-part of Ser. No. 942,616, Sep. 15, 1978, Pat. No. 4,252,772.

[51] Int. Cl.³ .................. B01D 7/00; B01D 59/02; C07D 307/89
[52] U.S. Cl. .......................................... 55/82; 55/209
[58] Field of Search .......................... 55/27, 80–82, 55/209, 269, 344; 422/244; 62/12; 165/2, 61, 108, DIG. 12, DIG. 16, 104.26; 260/346.7, 706

[56] References Cited

U.S. PATENT DOCUMENTS

| | | | |
|---|---|---|---|
| 1,725,906 | 8/1929 | Gay | 165/DIG. 12 |
| 1,842,263 | 1/1932 | Gobert | 55/82 |
| 2,076,033 | 4/1937 | Kniskern | 422/244 |
| 2,455,314 | 11/1948 | Dietzsch | 55/82 |
| 2,590,145 | 3/1952 | Aronson | 62/12 |
| 2,665,840 | 1/1954 | Powell | 165/108 |
| 3,602,429 | 8/1971 | Levedahl et al. | 165/104.26 |
| 3,766,971 | 10/1973 | Baum | 55/82 |
| 4,033,406 | 7/1977 | Basiulis | 165/104.26 |
| 4,062,871 | 12/1977 | Gehrken et al. | 422/198 |
| 4,127,163 | 11/1978 | Reti | 55/82 |
| 4,252,772 | 2/1981 | Way | 55/82 |

OTHER PUBLICATIONS

Ricci, Larry, CPI Niche for Heat, Chemical Engineerng, Jan.1978.
Air-to-Air Heat Recovery with Thermoscoil ™ reduces Energy Consumption, Isothermics, Inc., Mar. 1977, ISO-5-CC-2.

*Primary Examiner*—David L. Lacey

[57] ABSTRACT

Sublimate vapors are recovered from gases in a heat-pipe exchanger system, operating alternately in a condensing mode and a melting mode, for condensing on the exchanger tube surfaces such sublimable vapors as phthalic anhydride, maleic anhydride, naphthalene and fatty acids from gases containing said vapors thereof during the condensing mode, and for melting out the accumulated sublimate solids during the melting mode. Multiple, such as two or more units may be used to provide continuous processing of the sublimate vapor-laden gas stream, at least one operating in the condensing mode while simultaneously at least one may operate in the alternate mode. The cooling of opposite heat-pipe exchanger ends to recover sublimate solids is economical and efficient with ambient air, either alone or with some warm recycle exchanger air to adjust the cooling temperature; and the heating to melt out the accumulated solids is effective with heated air or hot waste gases, such as combustion gases, preferably by incineration of residual sublimate tail gas from which the sublimate was condensed, or other hot combustion gases, but other sources of heating the air or gases may be optionally substituted. Important advantage is present in superior heat exchange efficiency using the heat-pipe exchanger for this service, in the ease of switching from heating to cooling of such exchangers for alternate operation in both condensing and melting modes, in the elimination of intermediary heat transfer media and the separate auxiliary equipment required for the heating and cooling cycles, in the utilization of waste heat from combustion gases, and in the great economy for sublimate storage tank vent condensers through elimination of both cooling water and steam requirements.

10 Claims, 1 Drawing Figure

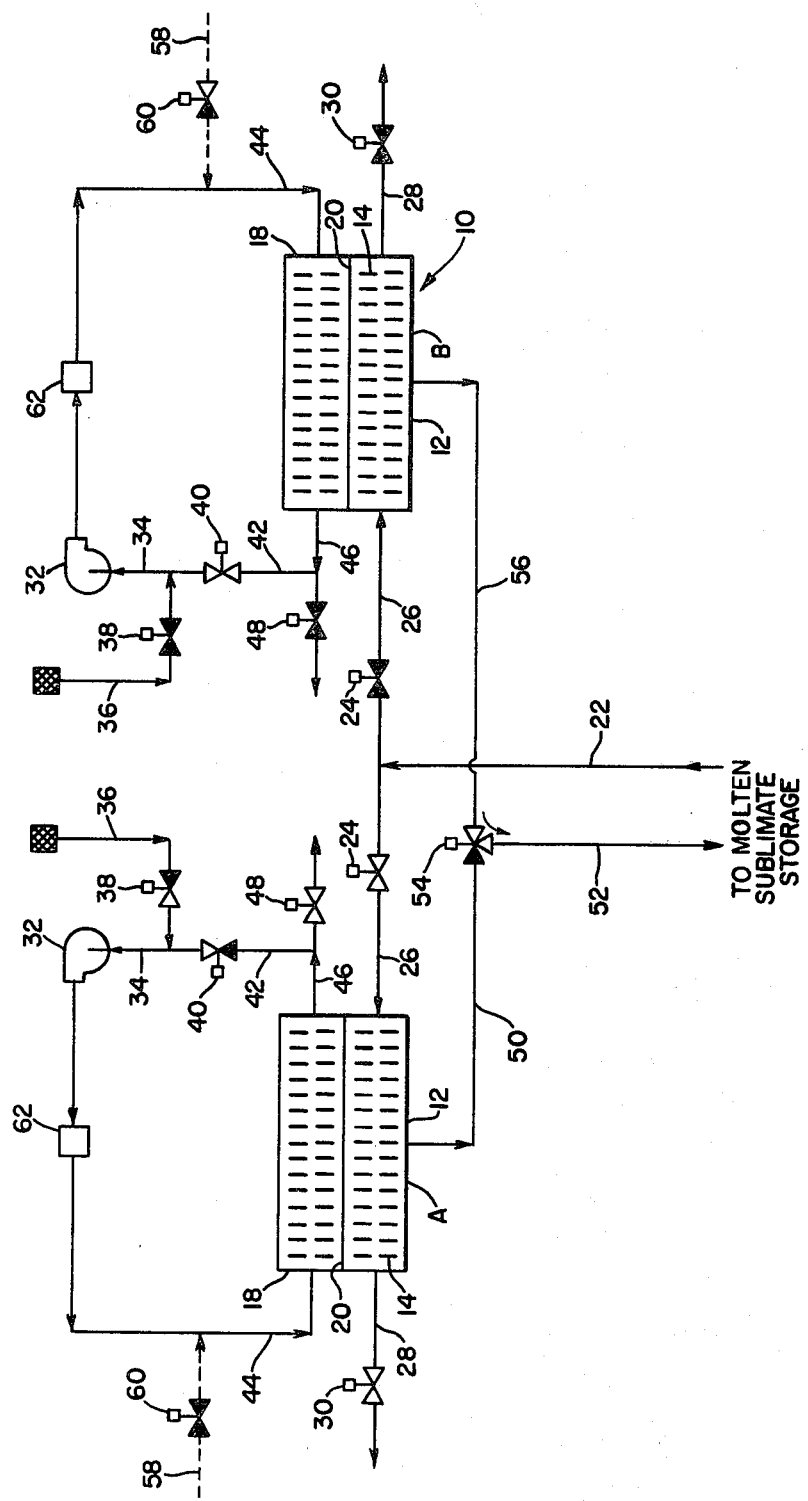

PROCESS FOR THE RECOVERY OF VAPORIZED SUBLIMATES FROM GAS STREAMS

This application is a continuation in part of my copending application, Ser. No. 942,616, filed Sept. 15, 1978, now U.S. Pat. No. 4,252,772, issued Feb. 24, 1981.

This invention relates to the recovery of sublimate vapors by condensation from gas streams, either as formed as a product of a chemical reaction, or as generated by any manufacturing process, or as released in the vent stream from storage tanks which contain the molten sublimate, in a heat transfer system of improved efficiency. More particularly, the invention relates to recovery of such sublimate vapors in a heat-pipe exchanger system, comprising a pump of heat pipes which in alternate operation condense the sublimate vapor to the solid state in one mode, and in another mode melt out the condensed solid. The heat-pipe exchanger system may be a multiple assembly of heat-pipe exchangers with one or more units operating in the condensing mode, while simultaneously the other unit or units operate in the melting mode, the units being cyclically alternated.

This system operates with great heat economy both with the more efficient exchanger system and by using ambient air as the cooling medium for the condensation operation and by using heated air or waste gases as the heating medium for the melting operation. The process hereof provides a more efficient method for the recovery of sublimate vapors such as phthalic anhydride, maleic anhydride, naphthalene, fatty acids, and like sublimable solid substances, and is greatly improved in economy over the prior art practices. The heat-pipe exchanger, although known per se as a type of heat exchanger, has not been used in the manner described for the recovery of such sublimates from the vapor state.

In particular, the alternate use of ambient air and hot air or gases for the cooling and heating modes provides a complete system for sublimate recovery without the need for a separate circulating water or other low temperature heat transfer medium to cool the gas and condense the sublimate, or steam or other high temperature heat transfer medium to melt out the recovered solids, so the heat exchanger system can be located and operated not only without these auxiliary heat transfer media systems, an important economy in itself, but also can be located in places where cooling water and steam are unavailable or costly.

PRIOR ART

The present methods used for the recovery of phthalic anhydride (PA) from gas streams provide a good example of prior art practices. The condensation of PA to a solid state is typically performed in shell and tube heat exchangers, or in arrangements of tube bundles in large enclosures with alternate cooling and heating of the tube surfaces by passage of a heat transfer medium through the tubes, one unit of which cools the gas stream to condense the PA vapor on the tube surfaces, and after selected periods the unit is alternated to the other mode of passing a second heat transfer fluid through the tubes at a temperature high enough to melt the PA.

In the case of such anhydride, there are several types of gas streams, and particularly there are three types of phthalic anhydride gas streams conventionally to be treated, the so-called (a) reaction gas stream formed in catalytic oxidation of naphthalene or o-xylene; (b) vent gas stream which emanates from PA storage tank breather vents; and (c) any manufacturing process gas stream that generates PA-laden vapors, each posing the problem of condensing the gaseous phthalic anhydride to solid form, and the subsequent warming of that solid condensate to recover the solid phthalic anhydride in molten form.

Particularly for phthalic anhydride reaction gas, the initial temperature of the PA gas stream is in the approximate range of 135°–250° C. and the exit gas temperature to which the gas stream is cooled is usually in the range of 45°–75° C., preferable to about 55°–65° C. Vent gases reach a lower entering temperature, such as 135°–165° C. with the desired exit gas temperature in the range of 40°–60° C. The process gas streams typically have an entering temperature in the range of 135°–200° C., depending upon the source of the process gas. Consequently, for the stated low exit temperature the exchanger surfaces at the outlet end should be maintained in the range of about 35°–60° C. with higher values applicable to reaction gas and lower values to vent and process gas streams.

In the case of other types of sublimates, the entering temperature will be determined by the particular reaction or manufacturing process, or storage tank temperature, but generally will be 0°–75° C. higher than the melting point of the material. The exit gas temperature is then fixed by the desired recovery efficiency, or by the allowable concentration of the sublimate vapor in the exit gas stream. These criteria when translated to an allowable vapor pressure of the sublimate in the gas stream enable the determination of the required exit temperature, which in the case of sublimates is always lower than the melting point of the material.

The tube surface temperature of the exchanger required for melting the deposited sublimate solids is generally in the range of about 2°–70° C. higher than the melting point, depending on the concentration of impurities that would tend to raise the melting point of the pure material. Merely by considering the extreme temperatures to be needed in each exchanger operation from low to high as stated, in the present practice separate systems are required for the two levels of heat transfer media to meet these two ranges, e.g., in the case of phthalic anhydride, from a low of 35°–60° C. to a high of 135°–190° C. These separate low temperature and high temperature fluid circulating systems that are needed for conventional exchanger practice typically depend on cooled water and high pressure steam, or a cold and a hot circulating fluid, and that was the practice of the prior art in making such temperatures practically available for handling these sublimate vapor streams in recovery processes.

AUXILIARY UNITS

Moreover, the low temperature circulating system must further be provided with means for dissipating the heat removed from the hot gas stream, and conventionally heat exchange with cooling water was employed for this, but the cooling water used also required a cooling tower for dissipating the heat. The high temperature heat transfer system, in contrast, required supply of high level heat to the circulating fluid, and this could be accomplished only by an indirect gas fired or oil heater, or by use of a boiler in the case of heating with steam.

It is clear that the facilities required in the prior art to alternately cool and heat the heat exchangers involved great initial investment, as well as high operating and maintenance costs. Moreover, conventional indirect exchangers of that type have low thermal efficiencies with accompanying low economy. In the case of phthalic anhydride reaction gas it is most uneconomical to utilize available waste heat in the tail gas incinerator exhaust usually associated with such systems. Furthermore, vent gas streams in most instances require processing at remote tankage areas where cooling water is not available and a cooling tower for this purpose must be installed. The isolated locations of such equipment items further present maintenance problems of such auxiliary elements complicated by the isolation.

Heat-pipe exchangers for the recovery of sublimates, according to the present invention, simplify the heat exchanger system by eliminating the need for an intermediary low temperature heat transfer system, such as cooling water or other medium, and impart greater thermal efficiency to the system, so that particularly in the case of phthalic anhydride reaction gas, the available waste heat from the reaction process is useful in the melting step to virtually eliminate the need for other fuel. In consequence, the present invention provides lower initial investment, lower operating costs and substantial fuel savings. Each of these objects is achieved in the novel heat exchanger system using the heat-pipe exchanger both in recovery and melting of sublimates applied in alternate operating modes. The system hereof uses ambient air directly as the cooling medium and either heated air or hot waste gas for the heating medium for melting the condensed solids in contrasting great efficiency and economy for this purpose.

The heat-pipe exchanger system hereof is uniquely adapted for recovery of sublimates from the various gas streams associated with reaction, manufacturing, or storage facilities to achieve these benefits. The term "heat pipe" as commonly understood and used herein refers to a conduit, pipe, duct or tube, usually but not necessarily circular in cross-section, and sealed at both ends to provide a closed circuit. The outer tube surfaces are usually but not necessarily finned or by other means extended. It includes a wick structure within the duct or tube and usually upon the inside surface, and the tube is evacuated and charged with a small quantity of a working fluid. Typical working fluids for these applications are the common fluorocarbon fluids such as R-11 and R-113, selected hydrocarbons or water. Heat absorbed at one end of the heat-pipe causes the working fluid to vaporize, and the vapor flows under the driving force of the slightly increased pressure to the cold end of the tube where it condenses and thereby releases its heat to the pipe wall. The circuit is completed by the condensed working fluid returning to the hot end of the heat pipe by capillary movement through the internal wick structure. A heat-pipe exchanger includes a substantial multiplicity of such heat-pipes, arranged so that all of the cold ends are exposed externally to the gas stream being heated, and the opposite hot ends are exposed to the gas stream from which heat is being extracted, in gas-to-gas heat exchange of the two streams, each conducted simultaneously through adjacent enclosures about opposite tube ends in countercurrent flow with the heat pipes in a bundle extending into separate enclosure ducts, one for each stream, and having a common dividing wall. The total heat-pipe exchanger consists of such tubes sized to accommodate the exchanger needs of the streams to be treated. The advantages of the heat-pipe exchangers applicable to sublimate recovery are:

1. They operate with small temperature difference between cold and hot ends of the heat-pipes under conditions of high heat transfer rates;
2. They have high thermal efficiency in gas-to-gas exchange at low pressure drops;
3. They have large surface areas that are available in heat-pipe bundles of resonable dimensions and usually through the use of extended surface or finned tubes for the accumulation of the condensed sublimate solids;
4. Bidirectional control of the aspect of heat-pipe operation is an inherent feature such that the heat transfer can be reversed by reversing the hot and cold ends, in this case by switching the hot and cold gas or air streams.
5. The working fluid contained in the sealed pipes can be readily selected as to be operable over the full temperature range of both condensing and melting steps from about 35°–225° C.

Because of these characteristics, ambient air can generally be used directly as a cooling gas stream for the condensing step. In cases where it is desirable for process reasons to limit the cooling stream to a minimum temperature, a portion of heated exit air is recycled to the blower and mixed with incoming ambient air to maintain the desired combined inlet temperature.

Again, heated air or hot waste gases are useful as the high temperature heating medium applied during the melting step. For this several options are available. One such is to recirculate through the air side of the heat-pipe exchanger heated air at a temperature above the melting point of the recovered sublimate, e.g., for phthalic anhydride in the range of about 150°–300° C. preferably 175°–225° C. The air may be heated by at least one of several alternate means such as by using a gas or oil fired in-line burner, or electrically using an electric resistance heater, or using a steam coil. A further option is available with reaction gas systems that employ a tail gas incinerator by using the incinerator exhaust gases adjusted to a suitable temperature range, e.g., 200°–300° C. for melting the phthalic anhydride. Typically, the incinerator exhaust gases will have a heat content sufficient to supply all of the necessary melt-step heat in a reasonable adjusted cycle time. Moreover, an auxiliary burner may be provided to pass combustion gases into the hot gas duct to supplement the heat as needed for the usual cycle time, or even to accelerate to shorter periods the melting time required to melt the sublimate using a higher temperature as provided by the extra heat, and periodically to remove other high melting impurities that may accumulate on the heat transfer surfaces for short excess-temperature heating periods. Still another option available for treatment of reactor gases, useful in the absence of a tail gas incinerator, is to use any available hot flue gas stream from an oil, gas or coal fired heater or steam boiler.

In storage tank vent gas applications, heating of the air for the melting step is most readily provided by use of an electric resistance heater, although a steam heater can also be used, with total air recirculation to minimize the energy requirement. In these several alternatives, the present method allows complete elimination of the need for separate cooling water systems, usefully serving remote tankage area locations, and it also makes possible elimination of steam supply and steam condensate systems.

Wide variations in methods for designing gas-to-gas heat-pipe exchangers for other services are known. In designing for condensation of the accumulated solid sublimates while maintaining the desired thermal efficiency and acceptable pressure drop, it is found that the number of tube rows may be increased in depth by a factor of 1.5 to 5, preferably 2 to 3 with respect to the usual gas-to-gas exchanger requirements. Alternatively, it is preferred to increase the face area of the condensing side of the exchanger by a similar factor, or to increase the face area in combination with an increase in the number of tube rows, to minimize pressure build up on the condensing side.

In the case of phthalic anhydride vent gas, process gas or reaction gas streams containing vaporized PA in the typical concentrations, ranging from 30–75 g/Nm$^3$ at a temperature in the range of 135°–250° C., such gas streams can be cooled with ambient air in a heat-pipe exchanger to an exit temperature of 45°–75° C., preferably 55°–65° C. with a PA recovery efficiency of greater than 99% and the condensed solid can be easily and efficiently melted off of the exchanger surfaces either by heated air or an exhaust gas stream or other heat alternatives listed above.

The invention is further described in relation to the drawings wherein:

The figure schematically shows, in plan view, an arrangement of a heat-pipe switch condenser system with one exchanger A in the condensing mode and the second heat-pipe exchanger B of the same system in the melting mode.

Each of the heat-pipe exchangers 10 are disposed in a divided housing 12 and 18. A number of heat pipes are disposed in a bundle 14, extending horizontally, or at a slight angle, from one housing 12 to the other housing 18, separated by a partitioning wall 20 which prevents any interchange of exchanger gases between housing 12 and housing 18. The incoming hot gas stream, either reaction gas, vent gas or process gas carrying recoverable vaporized sublimate enters through duct 22, the left valve 24 being opened and the right closed. The sublimate-laden stream passes into the housing 12 of exchanger A through that portion of exchanger bundle 14 contained therein, referred to as the "condensing side", at a temperature in the ranges stated above, leaving through the left duct 28, the left valve 30 being open. Alternatively, flow control may be accomplished entirely by valves 30 to eliminate the need for valves 24.

The left blower 32 draws ambient air through ducts 34 and 36 as well as recycle flow in line 42, the valves 38 and 40 being adjustably opened. The proportioned flows are adjusted by the settings of valves 38 and 40, to provide the inlet air at a temperature adjusted by recycle to housing 18 as cooling air to pass through the opposite portion of bundle 14, referred to as the "air side". The entering cooling air from line 44 at the left side of the exchanger thus passes in countercurrent flow to the sublimate-laden gas, and by the mechanism of heat transfer characteristic of heat pipes described above, cools the gas for condensing the sublimate to a solid, the residual gas leaving at 28. The heated air from the air side 18 leaves by way of line 46, the valve 48 being opened. In an alternate melting stage a duct 50 for removal of melted sublimate after first depositing in mode A operation is connected to a duct 52 through a valve 54 for disposal of the molten sublimate withdrawn to storage. The duct 54 is closed to exchanger A during the condensing cycle, while the sublimate is accumulated as solid therein.

As the hot entering sublimate-laden gas passes through the condensing side of the heat-pipe bundle 14, it transfers its heat to the heat pipes and condenses the sublimate vapor to the solid state. The heat extracted in gas cooling and in the condensation of the sublimate is conducted by vaporization of the heat-pipe internal working fluid to the opposite end of the tube bundle 14 where it is cooled and condensed by ambient air passing through housing 18. The lower temperature cooling air stream passing through the air side from line 44 cools and condenses the internal working fluid which then flows by capillary action through the wick structure therein, returning as liquid working fluid to the condensing side of heat-pipe bundle 14 contained in housing 12. A portion of the air heated in passage through the air side leaves by way of duct 46 and another portion controlled by valve 40 is recycled through line 34 for admixture with fresh ambient air to provide a temperature control for the entering ambient cooling air in line 44. During the cooling of the sublimate-laden reaction gas, the solid is condensed on the heat-pipe tube surfaces in the condensing side. Somewhat prior to the point at which the accumulated solids adversely affect the heat transfer or the pressure drop, the exchangers are each switched to the alternate mode, that is, mode A formerly condensing sublimate is switched to melting mode B and mode B formerly melting is switched to condensing. In this illustrative drawing, both left and right hand sides of FIG. 1 have similar exchangers simultaneously operating, one to condense sublimate and the other to melt and remove the condensed solids, shown in the figure as mode A on the condensing cycle and mode B on the melting cycle, which are alternatively switched to the opposite cycle periodically.

During the melting cycle exchanger B is isolated by valve 24, or valve 30 in the absence of valve 24, and the 3-way valve 54 is positioned to allow flow between ducts 56 and 52 for discharge of the melted sublimate. In the case of heat being provided by hot combustion gas or incinerator exhaust gas (combustion equipment and incinerator not shown), this hot gas stream flows through duct 58, valve 60 being open, enters the air side housing 18 of the exchanger B through line 44, and exits through valve 48, the recycle valve 40 being closed. The direction of heat transfer in the heat pipes is now reversed from that of the condensing mode. Heat is extracted from the hot gas stream passing through the air side in housing 18, causing the internal working fluid in the heat pipes to vaporize and to flow to the other side of the tube bundle contained in housing 12, on the external surfaces of which is deposited the solid sublimate condensed during the previous cycle. The condensing working fluid raises the temperature of the tube sufficiently to melt the accumulated solid as defined above. The condensed working fluid in the heat pipes then returns to the hot ends of the tube bundle in the air side to complete the internal flow cycle as described above.

In the alternate case of heat being provided by heater 62 (right side), which can be a gas or oil fired inline burner, a steam coil, or an electric resistance heater, blower 32 is used to recycle the heated air stream through duct 44, exchanger housing 18, returning to the blower through ducts 46 42 and 34, and valve 40, valves 38 and 48 being closed.

It will thus be observed that the system illustrated comprises equivalent exchangers, one of which is operating in condensing mode A simultaneously with the other exchanger operating in melting mode B. The system described herein, however, is not limited to using heat-pipe exchangers in pairs. In special cases of intermittent operation, a single exchanger may be employed. On the other hand, for large reaction gas installations, the system may comprise three or more exchangers, either in a balanced configuration with an equal number of exchangers alternately in mode A and mode B, or an unbalanced configuration with several exchangers in mode A and with a smaller number operating alternately in mode B on a shorter cycle time.

EXAMPLES

EXAMPLE 1

Reaction gas formed by catalytic oxidation of naphthalene flowing at a rate in the range of 10,000–20,000 $Nm^3/hr.$, typically $-17,500$ $Nm^3/hr.$, at a temperature of 145° C. and containing 48.4 $g/Nm^3$ of phthalic anhydride (PA) vapor is passed into a mode A operating heat-pipe exchanger as shown in FIG. 1. It is cooled in the exchanger to an outlet temperature of 60° C. to condense 99+% of the PA, depositing PA solids upon the tube surfaces of the condensing side of the heat-pipe exchanger. The ambient air circulated through the air side of the exchanger is flowing at a rate of 20,000–40,000 $Nm^3/hr.$, typically 36,000 $Nm^3/hr.$, adjusted to an exchanger inlet temperature of 38° C. by partial recycle of outlet air. The exchanger face dimensions on the condensing side of the exchanger are 3.66 m by 3.05 m and on the air side 2.44 m by 3.05 m. The tubes with an extended surface area of 0.59 $m^2/m$ are arranged in two banks of eight rows deep, each containing 208 tubes. The air blower has a power requirement of 10–20 KW. In mode B the exchanger for the melting step passes tail gas incinerator exhaust with a temperature of 204° C. at a rate of 10,000–20,000 $Nm^3/hr$, typically 17,000 $Nm^3/hr.$, and which is circulated through the air side of the heat-pipe exchanger to warm the tube surfaces to a temperature of 166° C. in about twenty minutes, at which temperature the deposited PA solids of mode A are melted and discharged from the exchanger. The total cycle time is about ninety minutes for deposition and melting out at these rates, forty-five minutes for each mode.

EXAMPLE 2

Vent gas from PA storage tanks containing 41 $g/Nm^3$ of vaporized PA, at a rate of 20–50 $Nm^3/hr.$, typically 34 $Nm^3/hr.$, and a temperature of 150° C., is cooled in mode A operation to 49° C. condensing 99+% of the contained PA on the dual heat-pipe exchanger system as shown in FIG. 1. It is operated with the following characteristics: Ambient air is circulated through the air side of the heat-pipe exchanger at a flow rate of 200–500 $Nm^3/hr.$, typically 345 $Nm^3/hr.$ adjusted to an inlet temperature of 38° C. by partial air recycle. The face dimension of the condensing side and the air side of the exchanger are 0.30 m by 0.22 m each. The heat pipes with an extended surface area of 0.59 $m^2/m$ are arranged in a single bank with a depth of fourteen rows for a total of forty-nine tubes. The maximum air power requirement is 0.3 KW. For the melting step mode B, the air is passed at 200–500 $Nm^3/hr.$, typically 360 $Nm^3/hr.$, at a temperature of 177° C. and circulated through the air side using an electric resistance heater as the source of energy for heating the air. The tube surfaces reach a temperature of 166° C. in about fifteen minutes. The PA condensing step of mode A is applied over a period of 4 to 8 hours, typically 6 hours, and the melting step is completed in forty-five minutes.

EXAMPLE 3

Vent gas from naphthalene storage tanks containing 71.7 $g/Nm^3$ of vaporized naphthalene, at a rate of 30–70 $Nm^3/hr$, typically 50 $Nm^3/hr$, and at a temperature of 100° C., is cooled in mode A operation to 40° C., condensing 96.3% of the contained naphthalene in the dual heat-pipe exchanger system as shown in FIG. 1. It is operated with the following characteristics: Ambient air is circulated through the air side of the heat-pipe exchanger at a flow rate of 300–700 $Nm^3/hr$, typically 550 $Nm^3/hr$, at an ambient air temperature of 30° C. The face dimension of the condensing side is 0.61 m by 0.35 m, and of the air side, 0.31 m by 0.35 m. The heat pipes with an extended surface area of 0.59 $m^2/m$ are arranged in a bank of 5 tubes high by 16 rows deep. For the melting step mode B, the air is passed at the above stated rate at a temperature of 120° C. and is recirculated through the air side using a steam coil heater for the source of energy for heating the air. The condensing step of mode A is applied over a period of 4 to 8 hours, typically 6 hours, and the melting step is completed in 45 minutes.

EXAMPLE 4

Vent gas from a manufacturing process containing 31.1 $g/Nm^3$ of vaporized maleic anhydride, at a rate of 30–70 $Nm^3/hr$, typically 55 $Nm^3/hr$, and at a temperature of 80° C., is cooled in mode A operation to 35° C., condensing 91.5% of the contained maleic anhydride, in a heat-pipe exchanger described in Example 3, and at the same air conditions. Melting is carried out at an air temperature of 100° C., with the recirculated air through the air side of the heat-pipe exchanger heated by an electric resistance heater. The condensing cycle is 4 to 8 hours, typically 6 hours, and the melting is completed in 45 minutes.

EXAMPLE 5

Vent gas from lauric acid storage tanks containing 0.41 $g/Nm^3$ of vaporized lauric acid, at a rate of 30 to 70 $Nm^3/hr$, typically 55 $Nm^3/hr$, and at a temperature of 70° C., is cooled in mode A operation to 35° C., condensing 94.3% of the contained lauric acid, which gives an exit concentration of 0.024 $g/Nm^3$, in the heat-pipe exchanger described in Example 3 and at the same air conditions. Melting is carried out at an air temperature of 85° C., with the recirculated air through the air side heated by an electric resistance heater. The condensing cycle is 4 to 12 hours, typically 8 hours, and the melting is completed in 45 minutes.

As thus described, sublimable solids are recovered in a two mode system, condensing the sublimate from commercially available streams, such as reaction, vent or process gases, by cooling in a heat-pipe exchanger or exchangers for deposition of the solid sublimate in yields of better than 90%, using ambient air or ambient air mixed for temperature adjustment with recycle air, and preferably simultaneously the deposited solid sublimate is separately melted in the same type of exchanger or exchangers, preferably in alternate cycles using ambient air for cooling and heated ambient air or combustion gases to melt the sublimate for recovery in a heat-pipe exchanger system with high operating efficiency.

The system may be modified, as will occur to one skilled in the art, for application of known variations of heat pipe structures and operations in the general exchanger art in the recovery of sublimates from gas streams, and it is intended that the description and examples be regarded as illustrative and not limiting, except as defined in the claims.

I claim:

1. In a method for recovering sublimate vapors from hot gas streams as formed in chemical reactions, manufacturing processes, storage tank vents or the like, in a heat-pipe exchanger system operative in a condensing mode and in a melting mode, said exchanger system comprising a pair of adjacent housings in which heat-pipe exchanger tubes are mounted horizontally so that the opposite tube ends extend into each housing, said pair of housings include an air-side housing through which cooling or heating fluid such as air or gas may be passed and a condensing-side housing through which sublimate-laden gas may be passed, each of said housings including means for independent flow control of hot and cold exchanger fluid therethrough, the method comprising the steps of, passing said hot gas stream through the condensing-side housing during the condensing mode to cool said gas stream and condense the contained sublimate vapors as a solid on the heat-pipe surfaces therein, simultaneously passing ambient air through the opposite air-side housing at a rate to remove the heat of cooling and condensation of said gas stream, and alternately switching to the melting mode by stopping the flow of gas through the condensing-side housing and passing heated air or hot gases through the air-side housing at a raised temperature sufficient to melt the condensed and deposited sublimate solids from the heat-pipe surfaces in said condenser-side housing and removing molten sublimate therefrom.

2. The method as defined in claim 1, wherein the gas stream carrying said sublimate vapors before passing through said condensing side housing of said heat-pipe exchanger is at an entering temperature higher than the melting point of the sublimate vapors which it carries and is cooled by passage through said heat-pipe exchanger to an exit temperature in the range of about 2°–70° C. higher than the ambient air temperature but low enough to condense and deposit said vapors upon the heat-pipe surfaces.

3. The method as defined in claim 1, wherein the said heated air or hot gas passed through said air-side housing of said heat-pipe exchanger for the melting of the deposited sublimate solids from the condensing side heat-pipe surfaces, is at a raised temperature sufficient to maintain said heat-pipe surfaces in the range of about 2°–70° C. above the melting point of the sublimate and substantially below its vaporizing temperature.

4. The method as defined in claim 1, wherein said cooling air stream by which said air side is cooled is a mixture of fresh ambient air and recycled air from the outlet of the air-side housing of said exchanger, said cooling air medium being adjusted to an inlet temperature to said exchanger in the range of 30° to 55° C.

5. The method as defined in claim 1, wherein the sublimate is melted and recovered by heating the exchanger tubes in said air side of said exchanger with a hot gas having an inlet temperature in the range of 50°–300° C.

6. The method as defined in claim 1, wherein the system consists of two or more of said heat-pipe exchanger systems with one or more operating in the condensing mode and simultaneously one or more exchangers operating in the melting mode, with cyclic switching of the operating mode of each exchanger to provide continuous processing of said gas streams for sublimate condensation and recovery therefrom.

7. The method as defined in claim 1 wherein the sublimate vapors in said feed gas comprise phthalic anhydride.

8. The method as defined in claim 1 wherein the sublimate vapors in said feed gas comprise maleic anhydride.

9. The method as defined in claim 1 wherein the sublimate vapors in said feed gas comprise naphthalene.

10. The method as defined in claim 1 wherein the sublimate vapors in said feed gas comprise fatty acids.

* * * * *

UNITED STATES PATENT AND TRADEMARK OFFICE
CERTIFICATE OF CORRECTION

PATENT NO.  :   4,391,617

DATED       :   July 5, 1983

INVENTOR(S) :   Peter F. Way

It is certified that error appears in the above-identified patent and that said Letters Patent is hereby corrected as shown below:

Column 1, line 16, "pump" should read -- group --.

*Signed and Sealed this*

*Eighth* Day of *November 1983*

[SEAL]

*Attest:*

GERALD J. MOSSINGHOFF

*Attesting Officer*     *Commissioner of Patents and Trademarks*